United States Patent [19]

York et al.

[11] Patent Number: 5,314,916

[45] Date of Patent: May 24, 1994

[54] B₂ ADRENEGIC AGONISTS AND USE THEREOF IN THE TREATMENT OF GLAUCOMA

[75] Inventors: Billie M. York, Fort Worth; Evan P. Kyba, Arlington, both of Tex.

[73] Assignee: Alcon Laboratories, Inc., Fort Worth, Tex.

[21] Appl. No.: 49,462

[22] Filed: Apr. 19, 1993

[51] Int. Cl.⁵ .................... A61K 31/22; A61K 31/24; C07C 69/03; C07C 69/757
[52] U.S. Cl. .................................. 514/542; 514/546; 560/46; 560/139
[58] Field of Search .................. 560/139.46; 514/546, 514/542

[56] References Cited

U.S. PATENT DOCUMENTS

| | | | |
|---|---|---|---|
| 4,010,202 | 3/1977 | Sugihara et al. | 564/164 |
| 4,104,402 | 8/1978 | Sugihara et al. | 514/654 |
| 4,559,361 | 12/1985 | Oka | 514/620 |
| 4,826,879 | 5/1989 | Yamamoto et al. | 514/657 |

FOREIGN PATENT DOCUMENTS 2514455  10/1975  Fed. Rep. of Germany.

OTHER PUBLICATIONS

Itoh, et al., "The Syntheses and β-Adrenoceptor Activities of N-Substituted 2-Amino-5,6-dihydroxy-1,2,3,4-Tetrahydro-1-naphthalenois," *Chem. Pharm. Bull,* vol. 25, No. 11, pp. 2917-2928 (1977).

Miyake, et al., "The Synthesis of 2,5-Diamino-6-hydroxy-1,2,3,4-tetrahydro-1-naphthalenol Derivatives," *Chem. Pharm. Bull,* vol. 25, No. 11, pp. 3066-3074 (1977).

Delgado, et al., "Synthesis and Conformational Analysis of 2-Amino-1,2,3,4-Tetrahydro-1-Naphthalenols," *Can J. Chem.,* vol. 66, pp. 517-527 (1988).

Motohashi, et al., "Crystal Structure of (±)-trans-2-Cyclobutylamino-5,6-dihydroxy-1,2,3,4-tetrahydro-1-naphthalenol Hydrobromide", *Chem. Pharm. Bull.,* vol. 28, No. 12, pp. 3656-3661 (1980).

Chemical Abstract 84(15): 105281e, (1975), Sugihara, et al.

Chemical Abstract 94(10): 75107q, (1980), Motohashi, et al.

*Primary Examiner*—José G. Dees
*Assistant Examiner*—Vera C. Clarke
*Attorney, Agent, or Firm*—James A. Arno; Gregg C. Brown

[57] ABSTRACT

Compounds having beta-2 adrenergic agonist activity and the use of these compounds in controlling intraocular pressure are disclosed. The compounds are believed to be useful in controlling intraocular pressure by increasing the outflow of aqueous humor. The compounds are considered to be less likely to cause cardiovascular side effects and various other side effects associated with stimulation of beta-1 receptors, relative to epinephrine.

9 Claims, No Drawings

B2 ADRENEGIC AGONISTS AND USE THEREOF IN THE TREATMENT OF GLAUCOMA

BACKGROUND OF INVENTION

The present invention relates to the fields of medicinal chemistry and ophthalmology. More specifically, this invention is directed to the provision of certain novel organic molecules which have an agonistic effect on beta-2 ("$B_2$") adrenergic receptors. The physiological effect of the subject compounds is useful in the treatment of various conditions, particularly glaucoma. The invention is therefore also directed to the provision of methods of treatment which employ one or more of the subject compounds and corresponding pharmaceutical compositions.

Glaucoma is a progressive disease which leads to optic nerve damage, and, ultimately, partial or total loss of vision. The causes of this disease have been the subject of extensive studies for many years, but are still not fully understood. The principal symptom of the disease is an elevated pressure within the eye caused by excess intraocular fluid (i.e., "aqueous humor").

The reasons why the excess fluid accumulates are not fully understood. It is known that the elevated intraocular pressure ("IOP") can be at least partially controlled by administering drugs which affect either the production of aqueous humor within the eye or the flow of aqueous humor out of the eye. The glaucoma therapies currently available primarily involve the use of drugs which act to reduce production of aqueous humor by the ciliary body of the eye. These therapies have been generally effective in the majority of patients. However, it is not always possible to control chronic elevations of IOP by reducing the amount of aqueous humor production, particularly in cases where obstructed outflow of aqueous humor is contributing to the excess fluid level and consequent elevation of IOP. Moreover, the reduction of aqueous humor production creates a risk that the avascular tissues of the eye, particularly the lens and the cornea, will be damaged due to an inadequate supply of nutrients and/or hydration caused by the reduced production of aqueous humor. The possible use of agents which increase the outflow of aqueous humor to control IOP has therefore been a topic of great interest to scientists engaged in glaucoma research.

The compounds of the present invention share some common structural characteristics with epinephrine, which is a well-known compound having both $B_1$ and $B_2$ agonist activity. Epinephrine has been widely used as a vasoconstrictor, cardiac stimulant and bronchodilator for many years. The use of epinephrine and related sympathomimetic compounds (e.g. phenylephrine, norepinephrine and dipivaloyl epinephrine) in ophthalmology is also well known. These compounds have been used both alone and in combination with other types of drugs to control IOP in glaucoma patients. While the precise mechanisms of physiological action are not totally understood, it is believed that the compounds help to control IOP by both reducing the production of aqueous humor through an action on the ciliary body of the eye and increasing the outflow of aqueous through an action on the trabecular meshwork.

Although epinephrine and the related compounds mentioned above have been a very useful and important part of the ophthalmologist's drug arsenal for many years, there are practical limitations of the utility of these compounds. For example, the ability of the compounds to control chronic or extreme elevations of intraocular pressure is limited. Moreover, the compounds stimulate both $B_1$ and $B_2$ adrenergic receptors. As a result, the use of the compounds to control intraocular pressure may produce undesirable stimulation of receptors in other tissues within the body, such as the tissues of the cardiovascular system. This stimulation of the cardiovascular system may cause significant side effects, such as a marked increase in blood pressure, tachycardia and arrythmia. These side effects are particularly troublesome in elderly patients, who frequently are already afflicted with high blood pressure or other cardiovascular abnormalities.

In view of the foregoing, there is a need for an improved therapy which provides for more potent control of elevated IOP. There is also a need for a therapy which controls elevated IOP without causing significant side effects in other systems of the body, particularly the cardiovasculature system. A therapy which controls IOP by means of increasing the outflow of aqueous humor, without adversely affecting the normal production of aqueous humor, is also highly desirable.

SUMMARY OF THE INVENTION

The present invention provides both new $B_2$ agonists and a new glaucoma therapy which is capable of controlling intraocular pressure without causing significant cardiovascular side effects. While applicants do not wish to be bound by any theory, it is believed that the $B_2$ agonists utilized in the present invention act to control intraocular pressure by increasing the outflow of aqueous humor. The increased outflow is brought about by an agonistic (i.e., stimulatory) effect on $B_2$ receptors within the trabecular meshwork of the eye. Unlike epinephrine and the related sympathomimetic compounds cited above, the compounds used in the present invention do not stimulate $B_1$ adrenergic receptors. The selective $B_2$ agonist activity of the present compounds is believed to eliminate potential for adverse cardiovascular side effects, as well as various other side effects associated with stimulation of $B_1$ receptors.

DESCRIPTION OF PREFERRED EMBODIMENTS

The compounds utilized in the present invention have the following formula:

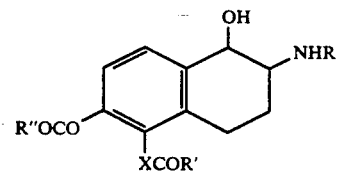

(I)

wherein:
X = O or NH;
R = lower alkyl lower branched alkyl, or lower cycloalkyl, preferably methyl, isopropyl or cyclobutyl;
if X = O, then R' = R" = lower branched alkyl or cycloalkyl, preferably tert-butyl; and
if X = NH, then R' = H, lower alkyl, branched alkyl or cycloalkyl, preferably hydrogen or methyl, and R" = lower branched alkyl or cycloalkyl, preferably tert-butyl.

These agents may be used as the free base or as pharmaceutically acceptable mineral acid or organic acid salts; the hydrochloride acid salt form is preferred.

Structurally related compounds, wherein the OCOR" group is OH and the XCOR' group is OH or NH₂, have been described by Itoh, et al., in scientific articles appearing in *Chem. Pharm. Bull.*, volume 25, at pages 2917-2928 and 3066-3074 (1977). The entire contents of those articles are hereby incorporated by reference in the present specification.

The compounds may be synthesized in accordance with the following reaction scheme:

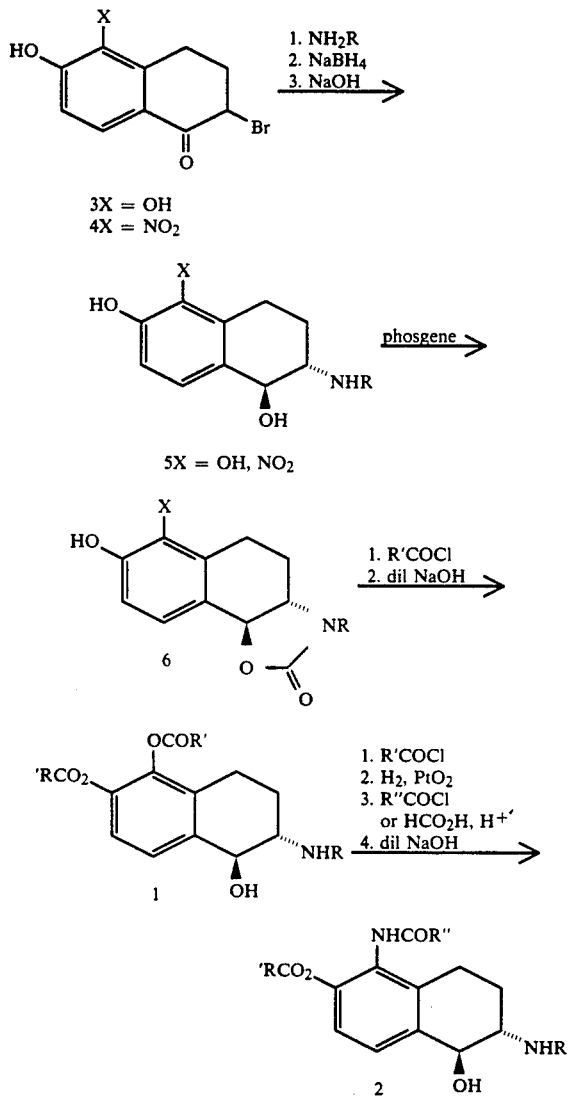

The synthesis commences with the bromo ketones 3 and 4. The catecol synthesis will parallel the aniline synthesis, excluding the reduction step. Amination, reduction and saponification produce the aminodiol 5. Protection of the vicaminoalcohol as the carbamate 6 can be accomplished in the presence of phosgene. Starting with 6, esterification and carbamate deprotection produce the diester 1. Starting with 6, esterification, selective reduction of the nitro group, amidation, and carbamate cleavage produce the ester 2.

The above agents, when conventionally formulated in ophthalmic pharmaceutical compositions in a concentration range of from about 0.01 to about 1.0 percent by weight based on the entire weight of the composition ("wt. %"), will serve to control IOP when applied topically to the affected eye(s). Dosage regimens will be determined by clinicians. The regimens will generally comprise topical application of one to two drops of an ophthalmic solution or suspension containing one or more compounds of formula (I), or a comparable amount of an ophthalmic ointment, gel or solid insert, one to four times per day.

The compounds of formula (I) may be included in various types of ophthalmic pharmaceutical compositions, in accordance with procedures and formulation criteria known to those skilled in the art. The compositions will contain one or more chemical preservatives to prevent microbial contamination of the compositions when dispensed in multiple dose containers. Preservatives which may be employed include benzalkonium chloride, thimerosal, chlorobutanol, methyl paraben, propyl paraben, phenylethyl alcohol, edetate disodium sorbic acid, and other agents known to those skilled in the art. Such preservatives are typically employed at a level of from about 0.001 to 1.0 wt. %. The compositions will also contain one or more buffering agents to maintain the pH of the compositions at or near the physiological pH of 7.4. Examples of buffering agents which may be utilized include phosphates, borates, citrates and carbonates. The tonicity of the compositions will preferably be at or near the tonicity of human tears (i e. , approximately 300-320 milliosmoles). The tonicity of the compositions can be adjusted, as needed, by adding sodium chloride, mannitol or other conventional and well-known agents. It may also be desirable to adjust the viscosity of the compositions, so as to improve the comfort of the compositions when topically applied to the eye. Viscosity-building agents which may be utilized include polyvinyl alcohol, tyloxapol, methylcellulose, hydroxypropyl methylcellulose, polyvinyl pyrrolidone, carboxyvinyl polymers, and various other agents known to those skilled in the art.

As with epinephrine, the compounds may be prone to oxidation. The use of an antioxidant, such as sodium metabisulfite, may therefore be necessary. Other precautions employed in connection with formulations containing epinephrine, such as protection from light by means of opaque containers, may also be necessary.

The following example is presented to further illustrate suitable formul at ions.

| Ingredient | Example Concentration (Wt %) |
|---|---|
| Compound of Formula (I) | 0.1 |
| Benzalkonium Chloride | 0.01 |
| Edetate Disodium | 0.01 |
| Hydrochloric Acid | 0.5 |
| Sodium Chloride | 0.4 |
| Sodium Metabisulfite | 0.15 |
| Hydrochloric Acid/Sodium Hydroxide | (as needed for pH adjustment) |
| Purified Water | Q.S. |

What is claimed is:
1. A compound of the formula:

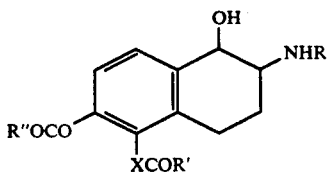

wherein:
X=O or NH;
R=lower alkyl, lower branched alkyl, or lower cycloalkyl;
if X=O, then R'=R"=lower branched alkyl or cycloalkyl; and
if X=NH, then R'=H, lower alkyl, branched alkyl or cycloalkyl, and R'=lower branched alkyl or cycloalkyl; or a pharmaceutically acceptable salt thereof.

2. A compound according to claim 1, wherein R is methyl, isopropyl or cyclobutyl; X is O; and R' and R" are both tert-butyl.

3. A compound according to claim 1, wherein R is methyl, isopropyl or cyclobutyl; X is NH; R' is hydrogen or methyl; and R" is tert-butyl.

4. A topical ophthalmic composition for controlling intraocular pressure, comprising an amount of a compound of the following formula effective to control intraocular pressure:

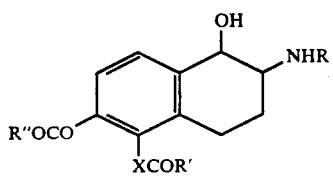

wherein:
X=O or NH;
R%32 lower alkyl, lower branched alkyl, or lower cycloalkyl;
if X=O, then R'=R"=lower branched alkyl or cycloalkyl; and if X=NH, then R'=H, lower alkyl, branched alkyl or cycloalkyl, and R"=lower branched alkyl or cycloalkyl, or a pharmaceutically acceptable salt thereof; and a pharmaceutically acceptable vehicle therefor.

5. A topical ophthalmic composition according to claim 4, wherein R is methyl, isopropyl or cyclobutyl; X is O; and R' and R" are both tert-butyl.

6. A topical ophthalmic composition according to claim 4, wherein R is methyl, isopropyl or cyclobutyl; X is NH; R' is hydrogen or methyl; and R" is tert-butyl.

7. A method of controlling intraocular pressure in a human patient, which comprises applying to the eye of the patient a therapeutically effective amount of an ophthalmic composition comprising an amount of a compound of the following formula effective to control intraocular pressure:

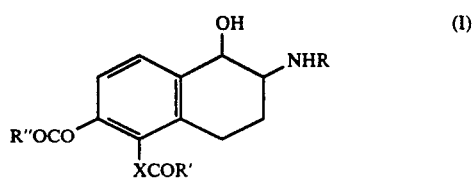

wherein:
X=O or NH;
R=lower alkyl, lower branched alkyl, or lower cycloalkyl;
if X=O, then R'=R"=lower branched alkyl or cycloalkyl; and
if X=NH, then R'=H, lower alkyl, branched alkyl or cycloalkyl, and R"=lower branched alkyl or cycloalkyl, or a pharmaceutically acceptable salt thereof; and a pharmaceutically acceptable vehicle therefor.

8. A method according to claim 7, wherein R is methyl, isopropyl or cyclobutyl; X is O; and R' and R" are both tert-butyl.

9. A method according to claim 7, wherein R is methyl, isopropyl or cyclobutyl; X is NH; R' is hydrogen or methyl; and R" is tert-butyl.

* * * * *